US006228117B1

(12) United States Patent
De Bruijn et al.

(10) Patent No.: US 6,228,117 B1
(45) Date of Patent: May 8, 2001

(54) DEVICE FOR TISSUE ENGINEERING BONE

(75) Inventors: Joost Dick De Bruijn; Yvonne Pearl Bovell, both of Den Haag; Jennigje Van Den Brink, Oegstgeest; Clemens Antoni Van Blitterswijk, Hekendorp, all of (NL)

(73) Assignee: IsoTis B.V., Bilthoven (NL)

( * ) Notice: Subject to any disclaimer, the term of this patent is extended or adjusted under 35 U.S.C. 154(b) by 0 days.

(21) Appl. No.: 09/116,177

(22) Filed: Jul. 15, 1998

(30) Foreign Application Priority Data

Jul. 16, 1997 (EP) .................................................. 97202214

(51) Int. Cl.$^7$ ...................................................... A61F 2/28
(52) U.S. Cl. .................................... 623/16.11; 623/23.61
(58) Field of Search .......................... 623/16, 919, 16.11, 623/23.61, 23.63

(56) References Cited

U.S. PATENT DOCUMENTS

| | | | |
|---|---|---|---|
| 4,963,489 | 10/1990 | Naughton et al. | 435/240.1 |
| 5,041,138 | 8/1991 | Vacanti . | |
| 5,226,914 | 7/1993 | Caplan et al. | 623/16 |
| 5,399,665 | 3/1995 | Barrera . | |
| 5,489,306 | 2/1996 | Gorski . | |
| 5,512,475 | 4/1996 | Naughton et al. | 435/240.243 |
| 5,522,895 | 6/1996 | Mikos . | |
| 5,569,250 | * 10/1996 | Sarver et al. | 606/69 |
| 5,629,186 | * 5/1997 | Yasukawa et al. | 435/177 |
| 5,688,531 | 11/1997 | Benayahu et al. | 424/574 |
| 5,908,784 | 6/1999 | Johnstone et al. | 435/372 |
| 5,972,703 | 10/1999 | Long et al. | 435/372 |

FOREIGN PATENT DOCUMENTS

| | | |
|---|---|---|
| 357155A1 | 3/1989 | (EP) . |
| 705609A2 | 4/1996 | (EP) . |
| WO 93/07916 | 4/1993 | (WO) . |
| WO 93/21858-A1 | 11/1993 | (WO) . |
| WO 93/21858-A6 | 11/1993 | (WO) . |
| WO 95/03011 | 2/1995 | (WO) . |
| WO 96/28539 | 9/1996 | (WO) . |

OTHER PUBLICATIONS

Gronthos et al., "The STRO–1+ Fraction of Adult Human Bone Marrow Contains the Osteogenic Precursors," *Am. Soc. of Hematology*, 84(12):4164–4173 (1994).

Kaku et al., "Method of Culturing Bone Marrow Cells, a Culturing Mixture, and Material for Transplantation to a Hard–Tissue Deficient Portion," JP Patent 7–194373, (abstract only), Aug. 1, 1995.

Ohgushi et al., "Heterotopic Osteogenesis in Porous Ceramics Induced by Marrow Cells," *J. Orthopaedic Research*, 7:568–578 (1989).

Ozawa and Kasugai, "Evaluation of implant materials (hydroxyapatite, glass–ceramics, titanium) in rat bone marrow stromeal cell culture," *Bomaterials*, 17(1):23–29 (1996).

Puleo et al., "Osteoblast responses to orthopedic implant materials in vitro." *J. Biomed. Mat. Res.*, 25: 711–723 (1991).

Radder et al., "Bone–bonding behavior of poly(ethylene oxide)–polybutylene terephthalate copolymer coatings and bulk implants: a comparative study," *Biomaterials*, 16(7):507–513 (1995).

Partial European Search Report for Application No. EP97202214, Dec. 16, 1997

* cited by examiner

*Primary Examiner*—Michael J. Milano
(74) *Attorney, Agent, or Firm*—Banner & Witcoff, Ltd.

(57) ABSTRACT

A device for bone tissue engineering is described which comprises a scaffold material consisting of a bioactive, osteoconductive and bone-bonding segmented thermoplastic copolyester and cultured osteogenic or osteoprogenitor cells, especially bone cells. The copolyester consists essentially of a multiplicity of recurring long-chain ester units and short-chain ester units, the long-chain ester units comprising from 35 to 80% by weight of the copolyester and being represented by the formula

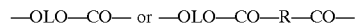

—OLO—CO— or —OLO—CO—R—CO— and the short-chain ester units being represented by the formula

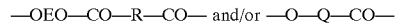

—OEO—CO—R—CO— and/or —O—Q—CO— wherein

L is a divalent group remaining after removal of terminal hydroxyl groups from a poly(oxyalkylene) glycol with an average molecular weight of between 300 and 3000;

R is a divalent group remaining after removal of carboxyl groups from a dicarboxylic acid having a molecular weight of less than 300;

Q is an alkylene group having 1–6 carbon atoms and/or a cyclohexylene of phenylene group; and E is an alkylene group having 2–6 carbon atoms.

20 Claims, No Drawings

DEVICE FOR TISSUE ENGINEERING BONE

The invention relates to a device facilitating cell growth, differentiation and subsequent osseous tissue generation in vitro and later in vivo, which comprises a porous, bioactive, osteoconductive and bone-bonding, polymer.

BACKGROUND

U.S. Pat. No. 5,226,914 (AI Caplan) discloses a method for treating connective tissue disorders by isolating and culturally expanding marrow-derived mesenchymal stem cells, adhering the cells onto the surface of a prosthetic device and implanting the prosthetic device containing the culturally expanded cells into the type of skeletal or connective tissue needed for implantation.

U.S. Pat. No. 5,399,665 (D Barrera) discloses the synthesis and applications of a hydrolytically degradable polymer useful in biomedical applications involving the interaction of cells with the polymer structure, by coupling peptides to the free amino groups of the polymers.

U.S. Pat. No. 5,041,138 (JP Vacanti) discloses methods and artificial matrices for the growth and implantation of cartilaginous structures and surfaces and the production of bioactive molecules manufactured by chondrocytes. Chondrocytes are grown in culture on biodegradable, biocompatible fibrous matrices until an adequate cell volume and density has developed for the cells to survive and proliferate in vivo, and the matrices are designed to allow adequate nutrient and gas exchange to the cells until engraftment and vascularisation at the site of engraftment occurs.

U.S. Pat. No. 5,522,895 (AG Mikos) discloses a biodegradable prosthetic template of a degradable polymer such as poly(lactic acid) or poly(lactic-co-glycolic acid) with a pore-former such as salt or gelatin, which template may be seeded with osteoblasts. The polymers used do not bind to bone and the osteoblasts are highly differentiated cells.

WO 96/28539 proposes a composition for growing cartilage or bone consisting of a biodegradable polymeric carrier such as polyglycolic acid or a polysaccharide containing mesenchymal stem cells. Mesenchymal stem cells are cells which are pluripotent, i.e. which can differentiate to various tissue types (muscle, cartilage, skin), while the polymers proposed do not bind to bone.

These prior art methods involve cells that are grown in the materials for the purpose of expansion or proliferation after which the materials containing the culturally expanded cells, are implanted at the site of engraftment. The prior art materials are degradable matrices, whether or not designed to couple peptides or biologically active moieties to serve to enhance binding of cells to the polymer, that mainly function as temporary devices for cell attachment. These prior methods therefore necessitate the production of connective tissues in vivo, while the prior materials function as a carrier for cell attachment and cell growth.

Surgical procedures related to bone tissue deficiencies vary from joint replacement, bone grafting and internal fixation, to maxillo-facial reconstructive surgery. From a biological perspective, the ideal material to reconstruct osseous tissues is auto-genous bone, because of its compatibility, osteoinductivity, osteoconductivity, and lack of immunologic response. However, the limitations of harvesting an adequate amount of autogenous bone, and the disadvantages of a secondary operation to harvest the autologous bone, make this "ideal" material far from ideal for many surgical procedures.

Alternatives are other bone-derived materials and man-made biomaterials. The first group concerns allogeneic and xenogeneic bone grafts. A problem is, that they exhibit the possibility of disease transfer such as HIV or hepatitis B, a higher immunogenic response, less revascularisation of the graft and manifest unreliable degradation characteristics.

The second group concerns man-made, alloplastic implant materials, or bio-materials, which are readily available in large quantities. The wide variety of biomaterials that are used in clinical applications can be divided into four major categories: metals, ceramics, polymers and composites, which all have their own characteristics. The most interesting alloplastic biomaterials for bone replacement are bioactive or osteoconductive materials, which means that they can bind to bone tissue. Bioactive materials can be found in all four of the above mentioned biomaterials categories and include polymers such as PEO/PBT copolymers, calcium phosphate ceramics such as hydroxyapatite and bioglasses or glass-ceramics.

Compared to autogenous bone, the main disadvantage of biomaterials is that, without added osteoinductive agents such as bone morphogenetic proteins, they are not osteoinductive and therefore do not have the ability to actively induce bone formation. Although this can be overcome by adding osteoinductive growth factors to the materials, difficulties still exist to gradually release these factors from the biomaterial surface over a prolonged time period, which is needed to have a sufficient biological response.

This is why there is a need for another approach for the treatment of osseous defects, which combines cultured autogenous tissues with biomaterials, in so-called biomaterial-tissue hybrid structures. Although the combination of cultured cells with biomaterials to form biomaterial-cell composites may also be advantageous in that the cultured cells, after implantation, can give rise to the formation of a tissue, we describe herein an invention of a device in which cells are cultured to produce an extracellular matrix, after which this biomaterial-tissue hybrid is implanted at the site of engraftment.

DESCRIPTION OF THE INVENTION

The present invention concerns a device made up from a polymeric material that is bicompatible, osteoconductive and bone-bonding (bioactive), that can be used to culture undifferentiated, differentiated, osteogenic or (osteo) progenitor cells that form a bone-like extracellular matrix in vitro, after which the polymer containing the biological extracellular matrix is placed or implanted at the site of engraftment. The uniqueness about the present invention is two-fold. In a first aspect, in contrast to the prior art methods, the material can calcify by itself during immersion in cell culture medium or post-operatively, or can be pre-calcified, thereby exhibiting bioactive and osteoconductive or bone-bonding properties that will improve tissue-material interaction. In the second aspect, undifferentiated, differentiated, osteogenic or (osteo)progenitor cells are grown in the bioactive, biodegradable polymeric matrix not only to expand, but to actively produce an extracellular matrix in vitro. Consequently, a hybrid structure encompassing a bioactive, biodegradable polymeric matrix and an already in vitro formed biological extracellular matrix is produced that can be used for engraftment in osseous defects or at sites where bone is needed. This invented hybrid structure can be seen as a flexible autogenous cultured bone graft which is unique.

The polymeric matrix can be constituted of a segmented thermoplastic bioactive, preferably biodegradable polymer, such as described in EP-A-357155 or WO-93/21858. The molecules of such segmented thermoplastic copolyester (polyesterether) consist essentially of segments of recurring long-chain ester units and segments with recurring short-chain ester units. The long-chain ester units preferably comprise 35–80% by weight of the copolytester (polyether) being represented by the formula

—OLO—CO—R—CO— and the short chain ester units being represented by the formula

—OEO—CO—R—CO— wherein
  L is a divalent group remaining after removal of terminal hydroxyl groups from a poly(oxyalkylene) glycol with an average molecular weight of between 300 and 500 or between 500 and 3000;
  R is a divalent group remaining after removal of carboxyl groups from a dicarboxylic acid having a molecular weight of less than 300; and
  E is an alkylene group having 2–6 carbon atoms.

Examples of the alkylene group in the poly(oxyalkylene) glycol of L include ethylene, 1,2-propylene, 2-hydroxy-1,3-propylene and butylene, poly(oxyethylene) glycol being preferred, especially polyoxyethylene on average consisting of 7 or 8 or more, up to about 70 oxyethylene units. The dicarboxylic acid of R may be aliphatic such as succinic, maleic, fumaric, glutaric, adipic, or preferably alicyclic such as cyclohexane-dicarboxylic, but most preferably it is aromatic such as isophthalic and terephthalic acid, which may be ring-substituted by e.g. hydroxy, alkyl, alkoxy, halogen and acyloxy, as well as dicarboxylic acids of, optionally ring-substituted, naphthalene, tetraline, biphenyl, diphenylmethane, diphenyl ether or diphenyl sulphone; terephthalic acid is especially preferred. A preferred example of alkylene in E is 1,4-butylene.

Alternatively, the molecules of such segmented thermoplastic copolyester consist of two or three blocks, one of these blocks being represented by the formula —O—L—, —O—L—O—CO— or —O—L—O—CO—R—CO— and the other blocks containing recurring units represented by the formula —O—Q—CO— and optionally units represented by the formula —O—E—O—CO—R—CO—, wherein Q is an alkylene group having 1–6 carbon atoms optionally linked or a cyclohexylene or phenylene group or a combination thereof. Examples of the groups Q include methylene, ethylidene, ethylene, 1,3-propylene, 1,5pentylene, 1,4-cyclohexylene, p-phenylenemethylene and p-ethylenephenylene.

According to one embodiment of the invention, the scaffold material is formed as a flexible sheet or structure. According to another embodiment, the material is formed as a rigid sheet or structure, The scaffold material may also advantageously be formed from weaved or intertwined fibres by a weaving, compressing or sintering process. The device may further suitably comprise filler materials such as calcium phosphates, bioactive glasses or glass ceramics in needle-shaped, fibre or granular form. The device of the invention and the method of producing it are further defined in the appending claims.

An advantage of the present technique is not only that a more organised tissue is produced in vitro prior to its implantation in vivo, which may give rise to a more rapid healing, but also that the implanted biomaterial-tissue hybrid exists of a surface that is covered by an extracellular matrix produced by the cultured cells. With regard to osseous tissues, and irrespective of the carrier material used (osteoconductive or not), this matrix will provide the biomaterial-tissue hybrid with a unique combination of both osteo-conductive and osteoinductive properties. In order to facilitate sufficient in vitro cell growth, matrix production and biomaterial-to-matrix bonding, the device should have bioactive or osteoconductive properties. The device according to this invention exhibits these properties, which makes it unique. Said bioactive or osteoconductive properties can be obtained via spontaneous calcification of the PEO/PBT carrier material after immersion in culture medium or post-operatively, or it can be improved or enhanced via the use of a pre-operative calcification method utilising calcification solutions, or by the use of a bioactive filler material, such as needle-shaped carbonate-apatite or hydroxyapatite (i.e. calcium phosphates, bioactive glasses or glass ceramics).

The osteoinductive properties of the biomaterial-tissue hybrid is shown in the appending examples and is the result of either in vitro formed extracellular bone matrix with osteoinductive proteins, the presence of the osteogenic cells, or a combination of these two. In order to speed up proliferation, differentiation and extracellular matrix production by the cultured cells, the device could also be filled with osteoinductive factors, growth factors or other biologically active agents.

Besides osteoconductive properties, the device should have an open pore branching network, composed of a biocompatible and ideally biodegradable biomaterial, that is configured in an arrangement that provides for the diffusion of nutrients, oxygen and waste products. The device could be both biodegradable or non-biodegradable.

The structure of the material is a non-porous or partially or fully porous scaffold, three-dimensional matrix, or (elastic) film. Porosity can be obtained as a result of ordered fibres, fibre meshes (e.g. weaving) or open cell foams (e.g. as a result of salt addition), but is not limited to these processes.

The device according to the invention can be used for a variety of surgical treatments where osseous generation or regeneration is needed. These include all bone defects in orthopaedics, maxillofacial surgery, dentistry and any other disciplines where osseous (re)generation is required. The device can also be used for guided tissue regeneration membranes in e.g. dentistry.

EXAMPLE 1

Rat Bone Marrow Cell Cultures on PEO/PBT Copolymers

Objective
  The objective of this experiment was to examine the formation of a mineralized extra-cellular matrix on PEO/PBT copolymers.
Materials
  55/45 PEO/PBT; 2 mm thick dense discs
  60/40 PEO/PBT copolymer; 0.8 mm thick dense discs
  30/70 PEO/PBT copolymer; 0.8 mm thick dense discs
  Prior to cell culture, all samples were rinsed in distilled water, dried at 37° C. and sterilised by gamma irradiation.
Method
  Cell Culture
  Bone marrow cells were isolated from the femora of young adult Wistar rats. In brief, the femora were washed 3 times in α-Minimum Essential Medium (α-MEM) containing ten times the normal concentration of antibiotics. The epiphyses were subsequently removed and each diaphysis was flushed out with 15 ml α-MEM containing 15% foetal bovine serum, antibiotics, 10 mM β-glycerophosphate, 50 μg/mt ascorbic acid and $10^{-8}$ M dexamethasone. The cell suspensions containing undifferentiated, differentiated and osteoprogenitor cells, were subsequently pooled and carefully resuspended by aspiration with a syringe and 21G needle. From this cell suspension, 200 μl droplets were inoculated onto the various materials, which were then incubated at 37° C./5% CO2 for several hours to allow cell attachment. Culture medium (as above) was subsequently added so that the samples were submerged; the culture plates were then replaced in the incubator. The cultures were refed three times weekly for 3–4 weeks.

Following the culture period, the samples were rinsed in phosphate buffered saline and fixed in 1.5% glutaraldehyde in 0.14 M cacodylate buffer for at least 24 hours. Following fixation, the samples were examined using light microscopy, scanning electron microscopy or transmission electron microscopy.

Light Microscopy (LM)

Following fixation, samples for LM where rinsed in 0.14 M cacodylate buffers dehydrated through a graded ethanol series and embedded in glycol methacrylate resin. Following polymerisation, 2–3 μm sections were prepared, which were then stained with toluidine blue, Alizarin red or von Kossa.

Scanning Electron Microscopy (SEM)

Following fixation, samples were rinsed in 0.14 M cacodylate buffer, dehydrated and critical point dried. Prior to either gold or carbon coating, the overlying cell multi-layers were removed. The samples were subsequently examined using scanning electron microscopy, back scatter electron microscopy (BSEM) and X-ray microanalysis (XRMA).

Transmission Electron Microscopy

Following fixation, samples were rinsed in 0.14 M cacodylate buffer, post-fixed in 1% osmium tetroxide/potassium ferrocyanate (1:1) in cacodylate buffer, dehydrated and embedded in Epon. Ultrathin sections were prepared and examined either unstained or after contrast staining with uranyl acetate and lead citrate.

Backscatter Electron Microscopy (BSEM)

Following TEM sectioning, a selection of Epon tissue blocks were processed for BSEM. The blocks were polished with 4000 grit silicon carbide sandpaper, rinsed with 70% ethanol, dried and carbon-coated. The samples were examined using a scanning electron microscope in backscatter mode, at 20 kV.

Results

Using light microscopy, it could be seen that the materials were biocompatible, in that no adverse tissue reactions were observed. Calcification, as a result of incubation in culture medium, was observed in the 55/45 and 60/40 materials although this phenomenon was not seen with the 30/70 copolymer. The presence of a mineralized extracellular matrix that had been produced by the cultured osteogenic cells, was demonstrated on the materials using Von Kossa and alizarin red staining techniques for phosphate and calcium respectively.

SEM revealed the deposition of globular, calcium and phosphate containing accretions on the surface of the materials. Mineralized collagen fibres were seen in close association with these globular strictures. In some areas, this mineralized extracellular matrix had fused to form a continuous layer.

TEM showed and backscatter electron microscopy revealed interfacial continuity between calcified structures in the 55/45 and 60/40 material surfaces and the in vitro formed mineralized extracellular matrix. With the 30/70 copolymer, mineralized extracellular matrix was seen in direct contact with the material surface although a continuity between the two was not observed.

Conclusions

These results show that different compositions of PEO/PBT copolymers are biocompatible and can give rise to spontaneous calcification when immersed in tissue culture medium. Osteogenic cells cultured on the materials can form a bonelike mineralized extracellular matrix which forms a close continuity with the material in areas where it is calcified.

EXAMPLE 2

Rat Bone Marrow Cell Cultures on Precalcified PEO/PBT Copolymers and PEO/PBT Copolymer Composites with AW Glass Ceramic and Hydroxyapatite Objective The objective of this experiment was to examine the formation of a bone-like mineralized extracellular matrix on precalcified PEO/PBT copolymers and PEO/PBT composites.

Materials

55/45 PEO/PBT precalcified in calcification solution

55/45 PEO/PBT/AW glass ceramic composite 5, 9, 20 and 50% AW glass

55/45 PEO/PBT/amorphous HA composite; 10 and 20% aHA

Prior to cell culture, all samples were rinsed in distilled water, dried at 37° C. and sterilised by gamma irradiation.

Method

Precalcification of PEO/PBT Coplymers in Calcium Chloride/$Na_2HPO_4$ Solution

Materials for precalcification were incubated in 1M calcium chloride for 3 days at room temperature) rinsed briefly in distilled water and dried at 37° C. They were subsequently incubated in 1M $Na_2HPO_4$ for 3 days at room temperature, rinsed briefly in distilled water, dried at 37° C. and gamma irradiated prior to cell culture.

Scanning Electron Microscopy (SEM) of the Starting Materials

Cross-sections of the composite plates were sputter-coated with carbon and were examined using a scanning electron microscope at an accelerating voltage of 15 kV.

Cell Culture

Bone marrow cells were isolated from the femora of young adult Wistar rats. In brief, the femora were washed 3 times in αMinimum Essential Medium (α-MEM) containing ten times the normal concentration of antibiotics. The epiphyses were subsequently removed and each diaphysis was flushed out with 15 ml α-MEM containing 15% foetal bovine serum, antibiotics, 10 mM β-glycerophosphate, 50 μg/ml ascorbic acid and $10^{-8}$M dexamethasone. The suspensions, containing undifferentiated, differentiated and osteoprogenitor cells, were subsequently pooled and carefully resuspended by aspiration with a syringe and 21G needle. From this cell suspension, 200 μl droplets were inoculated onto the various materials, which were then incubated at 37° C./5% CO2 for several hours to allow cell attachment. Culture medium (as above) was subsequently added so that the samples were submerged. The cultures were refed three times weekly and were maintained for 2 and 3 weeks. Following the culture period, the samples were rinsed in phosphate buffered saline and fixed in 1.5% glutaraldehyde in 0.14M cacodylate buffer for at least 24 hours. Following fixation, the samples were examined using light microscopy and transmission electron microscopy.

Light Microscopy (LM) and Transmission Electron Microscopy (TEM)

Following fixation, samples were rinsed in 0.14M cacodylate buffer, post-fixed in 1% osmium tetroxide/potassium ferrocyanate (1:1) in cacodylate buffer, dehydrated and embedded in Epon. For light microscopy, 2–3 μm sections were prepared, which were then stained with toluidine blue or the calcium specific stain Alizarin red. For TEM, ultrathin sections were prepared, contrast stained with uranyl acetate and lead citrate and examined in a transmission electron microscope at an accelerating voltage of 80 kV.

Backscatter Electron Microscopy (BSEM) and X-ray Microanalysis (XRMA)

Following TEM sectioning, the Epon tissue blocks were processed for BSEM and XRMA. The blocks were polished with 4000 grit silicon carbide sandpaper, rinsed with 70% ethanol, dried and carbon-coated. The samples were examined using a scanning electron microscope in backscatter mode, with an X-ray microanalysis unit.

Results

Scanning electron microscopy of the composite starting materials showed a random distribution of both the AW glass ceramic and the aHA particles throughout the copolymer matrix. Light microscopy revealed that the materials were biocompatible, in that no adverse tissue reactions were observed. Cellular nodules were seen on the materials and alizarin red staining revealed the presence of a mineralized extracellular matrix on the PEO/PBT/AW glass composites, with the exception of the 2 week culture on the PEO/PBT/ 5% AW glass composite. In case of the precalcified PEO/ PBT copolymer, a continuous layer of mineralized extracellular matrix was observed on the surface of the material. TEM showed a close contact between the mineralized extracellular matrix and the material surfaces. XRMA demonstrated the presence of calcification in all materials, except the 5% AW glass composite after 2 weeks in culture.

Conclusions

These results show that biocompatible precalcified copolymers, or copolymer composites can be produced, on which bone marrow cells can be grown that have the capacity to form a bone-like mineralized extracellular matrix. The close relation between calcified areas in the precalcified copolymer or copolymer composites and the bone-like mineralized extracellular matrix, indicates the osteoinductive character of these materials.

EXAMPLE 3

Cell Culture System for In Vivo Bone Tissue Engineering in (porous) Ceramics and Polymeric Biomaterials Objective To examine whether in vitro formed mineralized bone-like tissue, when formed in (porous) ceramic and polymeric templates, exhibits osteoconductive and osteoinductive properties when implanted in non-osseous sites, in vivo.

Materials

Porous hydroxyapatite; 400 μm pore diameter 30% porosity; sintered at 1300° C. for 96 hours Porous 70/30 PEO/PBT copolymer sheet (PEO=1000 Dalton molecular weight), 2 mm thick dense layer and a porous layer, 300–600 μm pore diameter, (i) non-precalcified and (ii) precalcified with Simulated Body Fluid which mimics the inorganic composition of tissue fluids;

Method

Cell Culture

Bone marrow cells were isolated from the femora of young adult Fischer rats. The femora were washed 3 times in α-Minimum Essential Medium (α-MEM) containing ten times the normal concentration of antibiotics. The epiphyses were subsequently removed and each diaphysis was flushed out with 6 ml α-MEM containing 15% foetal bovine serum, antibiotics, 10 mM β-glycerophosphate, 50 μg/ml ascorbic acid and $10^{-8}$ M dexamethasone. The cell suspensions were subsequently pooled and carefully resuspended by aspiration with a syringe and 21G needle. These primary cells were either directly seeded onto the various samples (600 μl/sample) or were cultured in tissue culture flasks for 5–7 days until near confluency was reached. For the latter, the cells were rinsed in phosphate buffered saline on reaching confluency, followed by trypsinisation to detach the cells from the culture surface. These sub-cultured cells were then counted and seeded onto the materials at a concentration of $1-2 \times 10^5$ cells per sample. All cultures were maintained in α-MEM medium as described above, in a humidified atmosphere of 95% air/5% $CO_2$ at 37° C. The medium was changed after the first 24 hours to remove non-adherent cells and was further refreshed three times weekly. After 4 weeks in vitro, a selection of samples were implanted subcutaneously in rats (see below); the remaining samples were cultured for a further one to four weeks. Control materials were placed in cell free culture medium in order to examine possible medium mediated alterations of the samples.

Implantation Procedure

The selected samples were implanted in the backs of 250–300 gram male albino Fischer rats. The rats were anaesthetised, shaved and cleaned with 10% ethanol/iodine. Two subcutaneous pockets were created on each side of the spine and one implant was inserted in each pocket. Survival periods included 1 and 4 weeks, after which time the samples were retrieved and evaluated using light microscopy and scanning electron microscopy.

Fixation

Following the implantation periods, the rats were euthanised, and the samples were retrieved and fixed in 1.5% glutaraldehyde in 0.14M cacodylate buffer, pH 7.4, for at least 24 hours. In vitro samples were fixed in similar fixative. Following fixation, the samples were processed for the various evaluation techniques.

Light Microscopy (LM)

Following fixation, samples for LM were rinsed in 0.14M cacodylate buffer, dehydrated through a graded ethanol series and embedded in methyl methylacrylate resin. Following polymerisation, undecalcified 10 μm thick sections were prepared using a modified innerlock diamond saw; the section were stained with mathylene blue and basic fuchsin.

The remainder of the LM tissue blocks were subsequently processed for backscatter electron microscopy.

Backscatter Electron Microscopy (BSEM)

Following sectioning for LM, the tissue blocks were polished with 4000 grit silicon carbide sandpaper, rinsed with 70% ethanol, dried and carbon-coated. The samples were examined using a scanning electron microscope in backscatter mode, at 20 kV.

Scanning Electron Microscopy (SEM)

Following fixation, samples were rinsed in 0.14 M cacodylate buffer, dehydrated and critical point dried. The samples were subsequently examined using a scanning electron microscopy at 15 kV.

Results

Hydroxyapatite

After 4 weeks in vitro, a mineralized extracellular matrix had formed along most of the outer surface of the hydroxyapatite and after 8 weeks, the thickness of this layer had increased. After 4 weeks in vitro, followed by 4 weeks in vivo, bone formation was observed, both on the outer surface and in the ports of the material. This bone tissue was clearly distinguishable from the in vitro formed mineralized matrix, in that it had an organised structure with, for example, osteoblast seams and osteocytes in lacunae. In the control samples, without cultured cells, bone formation was not observed.

Non-precalcified and Precalcified PEO/PBT Copolymers

After 4 weeks in vitro, the formation of a mineralized extracellular matrix was observed in both materials. In the control samples, without cells, abundant calcification of the materials was observed at all evaluation times.

After 4 weeks in vitro, followed by 4 weeks in vivo, bone formation was observed in both the non-precalcified and precalcified materials. As with the HA, this bone tissue was morphologically more mature than the in vitro formed mineralized matrix. Mineralized extracellular matrix was not observed in any of the control cultures (without cells), which confirms the non-osteoinductive character of the material itself, while the material-cultured bone-like tissue hybrid exhibits osteoinductive properties. Degradation of the porous polymer was seen, in that small fragments were visible. This degradation did not give rise to an inflammatory response or any adverse tissue reactions.

Conclusions

The results show that rat bone marrow cells can be cultured in porous degradable biomaterials to produce an osteoinductive, osteoconductive hybrid material. Although the materials themselves do not give rise to osteoinduction, the presence of an in vitro formed bone-like extracellular matrix results in osteoinduction and de novo bone formation. This suggests that these materials can be used as carriers for bone tissue engineering. With the copolymer, a flexible autogenous cultured bone graft can be produced in vitro for implantation purposes.

What is claimed is:

1. A device for bone tissue engineering comprising a scaffold material including a bioactive, osteoconductive and bone-bonding segmented thermoplastic copolyesterether and osteogenic or osteoprogenitor cells.

2. The device of claim 1, wherein said copolyesterether includes a multiplicity of recurring long-chain ester units and short-chain ester units, the long-chain ester units comprising from 35 to 80% by weight of the copolyesterether and being represented by the formula

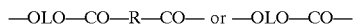

—OLO—CO—R—CO— or —OLO—CO— and the short-chain ester units being represented by the formula

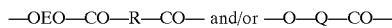

—OEO—CO—R—CO— and/or —O—Q—CO— wherein

L is a divalent group remaining after removal of terminal hydroxyl groups from a poly(oxyalkylene) glycol with an average molecular weight of between 300 and 3000;

R is a divalent group remaining after removal of carboxyl groups from a dicarboxylic acid having a molecular weight of less than 300;

Q is an alkylene group having 1–6 carbon atoms and/or a cyclohexylene or phenylene group; and E is an alkylene group having 2–6 carbon atoms.

3. The device according to claim 2, wherein said long-chain ester units constitute from 45 to 75% by weight of the copolyesterether.

4. The device according to claim 3, wherein said long-chain ester units are poly(oxyethylene) units and said short-chain ester units are poly(butylene terephthalate) units.

5. The device of claim 1, said scaffold material including a non-porous layer and a porous layer.

6. The device of claim 1, said scaffold material having interconnecting pores with a pore diameter of between about 50 to about 800 $\mu$m.

7. The device of claim 1, said scaffold material having an increase in pore size from 10 to 800 $\mu$m from one side of the device to the other.

8. The device of claim 1, wherein said copolyesterether is calcified.

9. The device of claim 1, said scaffold material in the form of a granulate or spheres with a size between about 1 and about 10 mm.

10. The device of claim 1, further comprising osteninductive factors, growth hormones, or other biologically active agents.

11. The device of claim 1, wherein said cells are selected from bone, bone marrow, cartilage, muscle tissue, fibrous tissue, skin, soft connective tissue or other connective tissues.

12. The device of claim 11, further comprising bone cells.

13. The device of claim 1, further comprising a mineralised, partially mineralised or non-mineralised extracellular bone matrix.

14. The device of claim 1, further comprising a bone matrix.

15. The device of claim 1 said scaffold material including a non-porous layer and a porous layer at either side of the non-porous layer.

16. The device of claim 1, said scaffold material having interconnecting pores with a pore diameter of between about 200 to about 500 $\mu$m.

17. The device of claim 1, said scaffold material in the form of a granulate or spheres with a size between about 2 and about 5 mm.

18. A biomaterial-tissue hybrid structure produced in vitro and being for use in treatment of osseous defects, the hybrid structure comprising:

a) a biocompatible, bioactive synthetic polymeric scaffold material having an exterious surface; and b) an osseous, extracellular matrix formed on the exterior surface of the polymeric scaffold materials from osteogenic or osteoprogenitor cells.

19. A biomaterial-tissue hybrid structure according to claim 18 wherein the scaffold material comprises a fibrous sheet.

20. A biomaterial-tissue hybrid structure according to claim 19 wherein the polymeric scaffold material comprises a biodegradable, osteoconductive, segmented thermoplastic copolyester ether.

* * * * *